(12) United States Patent
Menzenbach et al.

(10) Patent No.: US 7,186,728 B2
(45) Date of Patent: Mar. 6, 2007

(54) METHYLENE-4-AZASTEROIDS

(75) Inventors: Bernd Menzenbach, Jena (DE); Peter Droescher, Weimar (DE); Alexander Hillisch, Jena (DE); Walter Elger, Berlin (DE); Hans-Udo Schweikert, Bonn (DE); Klaus Schoellkopf, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/487,862

(22) PCT Filed: Aug. 28, 2002

(86) PCT No.: PCT/EP02/09587

§ 371 (c)(1),
(2), (4) Date: Aug. 6, 2004

(87) PCT Pub. No.: WO03/020744

PCT Pub. Date: Mar. 13, 2003

(65) Prior Publication Data

US 2004/0248921 A1    Dec. 9, 2004

(30) Foreign Application Priority Data

Aug. 28, 2001   (DE)   ............... 101 41 984

(51) Int. Cl.
*A61K 31/473*   (2006.01)
*C07D 221/18*   (2006.01)
(52) U.S. Cl. .................... 514/284; 546/77
(58) Field of Classification Search ........... 514/284; 546/77

See application file for complete search history.

(56) References Cited

U.S. PATENT DOCUMENTS 5,763,361 A * 6/1998 Harris et al. ............. 514/284

FOREIGN PATENT DOCUMENTS

| WO | 93 15104 A | 8/1993 |
|----|------------|--------|
| WO | 97 15558 A | 5/1997 |
| WO | 98 33506 A | 8/1998 |
| WO | 02 00681 A | 1/2002 |
| WO | 02 19971 A | 3/2002 |

OTHER PUBLICATIONS

Rasmusson et al: "Azasteroids as Inhibitors of Rat . . . " Journal of Medicinal Chemistry, American Chemical Society, Washington, US, vol. 27, No. 12, Dec. 1, 1984, pp. 1690-1701.

Brooks et al: "5alpha-Reductase Inhibitory and Anti . . . "Steroids: Structure, Function, and Regulations, Elsevier Science Publishers, New York, NY US, vol. 47, No. 1, 1986, pp. 1-19.

Rasmusson et al: "Azasteroids: Structure-Activity Relationships . . . " Journal of Medicinal Chemistry, American Chemical Society, Washington, US, vol. 29, No. 11, Nov. 1, 1986, pp. 2298-2315.

J.K.L. Tan: "Oral Contraceotives in the Treatment of Acne" Skin Therapy Letter, vol. 6, No. 5, Feb. 2001, pp. 1-8. (in English).

J.A. Miller et al: "Anti-Androgen Treatment in . . . " Brotish Journal of Dermatology 1986, 114, pp. 705-716. (in English).

R. Greenwood et al: "Acne: Double Blind Clinical and . . . " British Medical Journal vol. 291, Nov. 2, 1985, pp. 1231-1235 (in English).

Julianne Imperato-McGinley et al: "The Androgen Control . . . " Journal of Clinical Enfdocrinology and Metabolism, vol. 76, No. 2, pp. 524-528, 1993.

"Behandlung Der Alopecia. . . "http:haarerkrankungen.de/therapie/Aga_finasteridtherapie.htm, Admitted Prior Art (With English Translation).

* cited by examiner

*Primary Examiner*—Charanjit S. Aulakh
(74) *Attorney, Agent, or Firm*—Michael J. Striker

(57) ABSTRACT 17-methylene-4-azasteroid compounds of formula I:

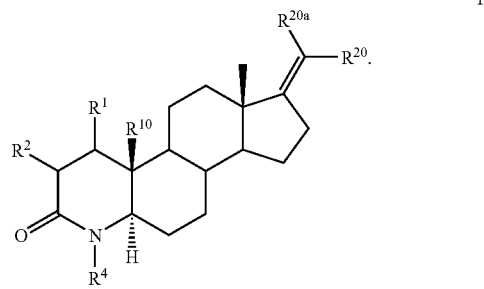

wherein $R^{20}$ denotes fluoro, chloro or bromo $R^{20a}$ denotes hydrogen, $R^{10}$ and $R^4$ each denote a hydrogen atom or a methyl group, and $R^1$ and $R^2$ each denote a hydrogen atom or together denote an additional bond, are useful for treating diseases or conditions caused by excessive androgen levels, such as acne, prostate diseases, alopecia and hirsutism, as well as gynecological conditions. Methods of synthesizing the new 17-methylene-4-azasteroid compounds are described.

10 Claims, 5 Drawing Sheets

METHYLENE-4-AZASTEROIDS

The present invention comprises novel 17-methylene-4-azasteroids of general formula I:

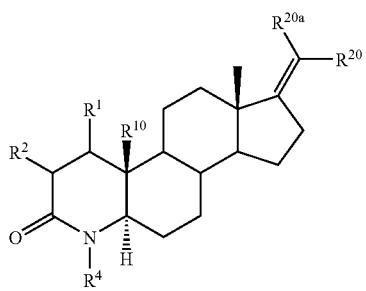

wherein
$R^{20}$ denotes fluoro, chloro, bromo, azido, cyano, thiocyanato, a $C_1$-$C_4$-alkyl or a hydroxy-$C_1$-$C_4$-alkyl group,
$R^{20a}$ denotes hydrogen,
$R^{10}$ denotes a hydrogen atom or a methyl group,
$R^4$ is selected from the group consisting of hydrogen and $C_1$-$C_4$-alkyl groups, and
$R^1$ and $R^2$ each denote a hydrogen atom or together denote an additional bond.

In preferred embodiments of these novel compounds $R^{20}$ and $R^{20a}$, independently of each other, each denote F, Cl, Br or CN, $R^{20a}$ may also be H and $R^4$ is H or Me.

Methods for preparing novel compounds and for producing pharmaceutical compositions thereof are described.

The compounds of the invention, 17-methylene-4-azasteroids, are new; their preparation and their biological activity have thus far not been described.

Preferred compound of formula I include
E-17-chloromethylene-4-aza-5α-estran-3-one,
E-17-chloromethylene-4-aza-5α-androstan-3-one,
E-17-chloromethylene-4-methyl-4-aza-5α-estran-3-one,
E-17-chloromethylene-4-methyl-4-aza-5α-androstan-3-one,
E-17-chloromethylene-4-aza-5α-estr-1-en-3-one,
E-17-chloromethylene-4-aza-5α-androst-1-en-3-one,
E-17-chloromethylene-4-methyl-4-aza-5α-androst-1-en-3-one,
E-17-bromomethylene-4-methyl-4-aza-5α-estran-3-one,
E-17-cyanomethylene-4-methyl-4-aza-5α-estran-3-one,
Z-17-(1')-chloroethylidene-4-methyl-4-aza-5α-androstan-3-one,
Z-17-(1')-chloroethylidene-4-methyl-4-aza-5α-estran-3-one,
Z-17-(1')-bromoethylidene-4-methyl-4-aza-5α-androstan-3-one and
Z-17-(1')-bromoethylidene-4-methyl-4-aza-5α-estran-3-one.

Another object of the present invention are pharmaceutical compositions containing as the active ingredient at least one 17-methylene-4-azasteroid of general formula I, and at least one of appropriate auxiliary agents and carriers.

The 17-methylene-4-azasteroid compounds of the invention are 5α-reductase inhibitors. Hence, they are suitable for the treatment of diseases caused by elevated testosterone levels and finally dihydrotestosterone levels in the blood and tissues.

Diseases induced by excessive androgen effects can also occur at normal blood testosterone levels if the conversion of testosterone to dihydrotestosterone in the tissues is elevated. This is the case, for example, in idiopathic forms of hirsutism (REF).

Progesterone plays an important role in the tight closing of the os of uterus (Mahendroo). The softening thereof before giving birth is a result of local 5α-reductase-induced degradation of progesterone to dihydroprogesterone, which is a very weak gestagen. By inhibiting the progesterone catabolism in this part of the uterus, the substances of the invention are therefore also suitable for preventing premature maturation and opening of the os of uterus.

5α-Reduced metabolites of progesterone (REF from Lancet) and other C21-steroids and the metabolites thereof formed in the body, for example allo-pregnanolone, can act as neurosteroids and can interact with neurosteroids. Disorders of this function can result in depression. Possible indications for the substances of the invention are prostate diseases, alopecia of the masculine type, acne and hirsutism as well as various gynecological clinical conditions such as the premenstrual syndrome. The appearance of 5α-reduced metabolites of progesterone in the CNS plays an important role in the onset of such conditions. Premature opening of the os of uterus can be induced by increased degradation of progesterone to dihydroprogesterone in this tissue. The substances of the invention are suitable for preventing this catabolism and thus the premature maturation of the cervix uteri. The substances of the invention can exert their action by inhibiting the 5α-reduction of testosterone or progesterone in the organs and tissues affected by this disorder. In addition, the blood levels of the 5α-reduced metabolites are lowered.

Moreover, the compounds of the invention constitute intermediates for the synthesis of other pharmacologically highly active steroid products.

The compounds of the invention are prepared as indicated in the appended method claims.

According to the invention, the 17-methylene-4-azasteroid compounds can be derived from the 17-methylene-steroids of general formula II and general formula VII.

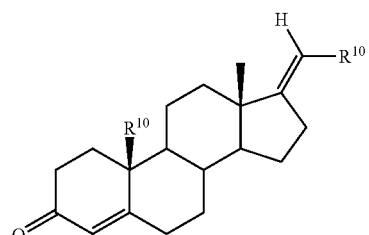

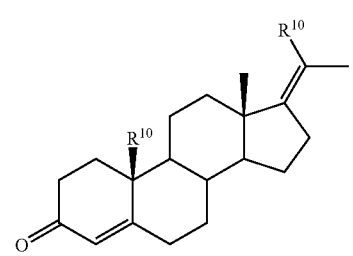

Compounds according to the invention are obtained by reacting compounds of general formula II in a known manner with NaIO$_4$ with catalytic mediation of KMnO$_4$ in a protic solvent, preferably tert.-BuOH, to form the 3,5-seco keto acid, cyclizing this acid with NH$_4$OAc in glacial acetic acid to form the unsaturated lactam and then reducing said lactam to the saturated lactam of general formula III with HCOOH/K$_2$CO$_3$ in DMF:

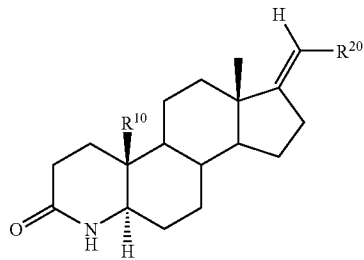

III further reacting the compounds of general formula III with MeI and NaH in a dipolar aprotic solvent, preferably DMF, to form the 4-methyl-substituted compounds of general formula IV:

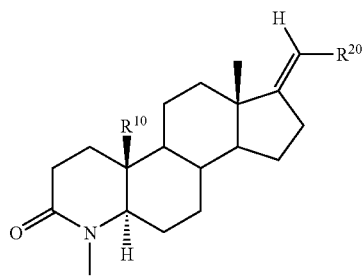

IV and reacting other compounds of general formula III by a silyl-mediated DDQ (2,3-dichloro-5, 6-dicyano-1, 4-benzoquinone) oxidation in a dipolar aprotic solvent, such as dioxane, to form the dehydrogenated lactams of general formula V:

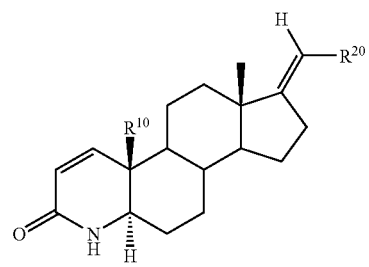

V

The compounds of general formula V, like the compounds of general formula III, are reacted with MeI and NaH to form the 4-methyl-substituted lactams of general formula VI:

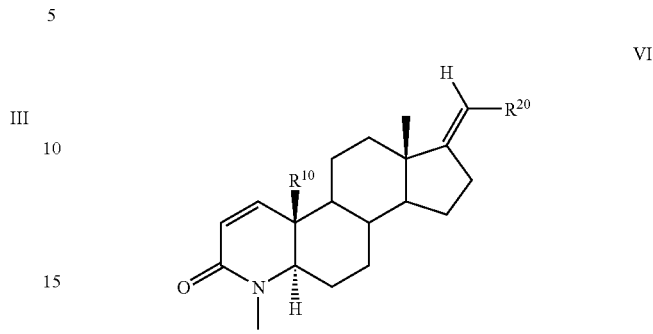

VI

Moreover, 17-methylene-4-azasteroid compounds according to the invention are obtained by subjecting compounds of general formula VII to the same chemical reactions as the compounds of general formula II, thus forming compounds of general formulas VIII, IX, X and XI.

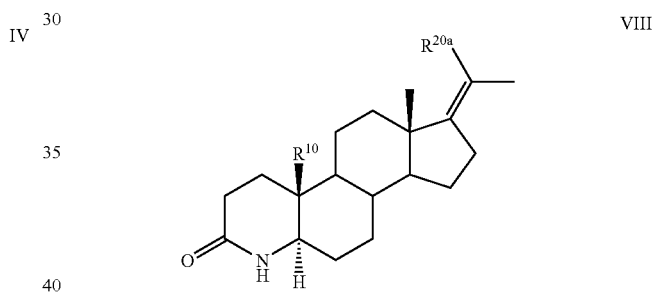

VIII

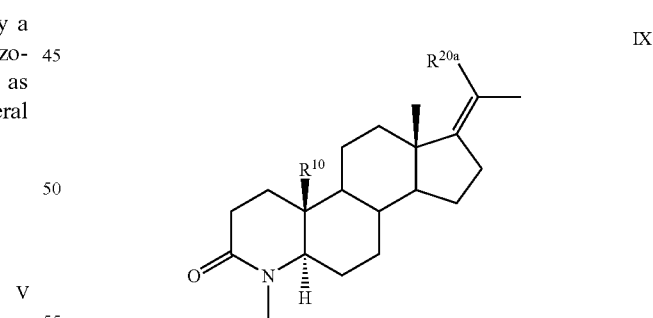

IX

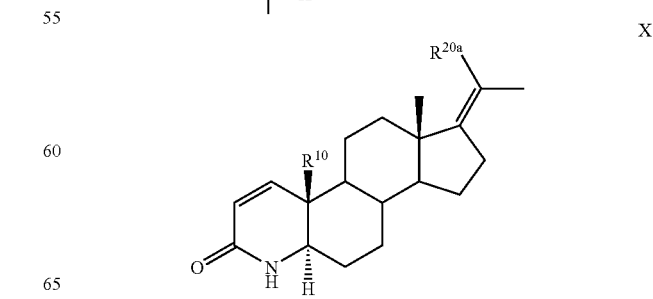

X

-continued

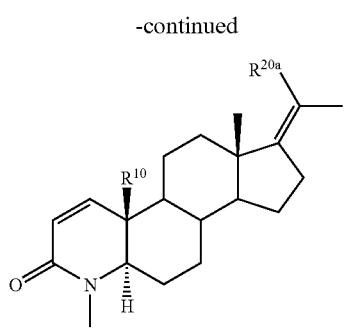

XI

BRIEF DESCRIPTION OF THE DRAWING

The objects, features and advantages of the invention will now be illustrated in more detail with the aid of the following description of the preferred embodiments, with reference to the accompanying figures in which.

RESULTS

Figure 1:
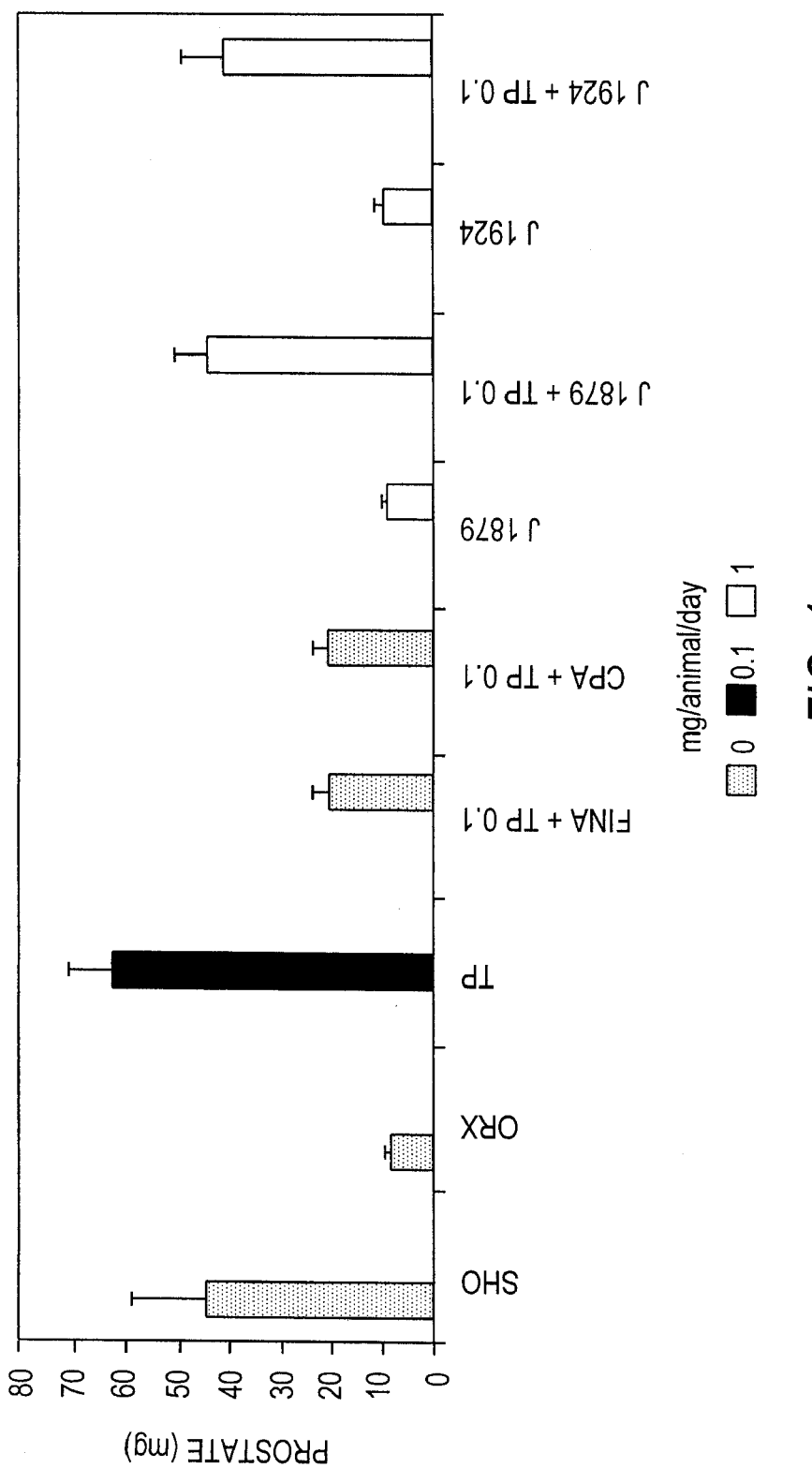
FIG. 1 is a graphical illustration comparing prostate weight in castrated infantile male rats after administration of two examples of the 17-methylene-4-azasteroid compounds according to the invention with prostate weight in the rats after administration of CPA and finasterides to demonstrate the improved antiandrogenic activity of the compounds according to the invention.
Figure 2:
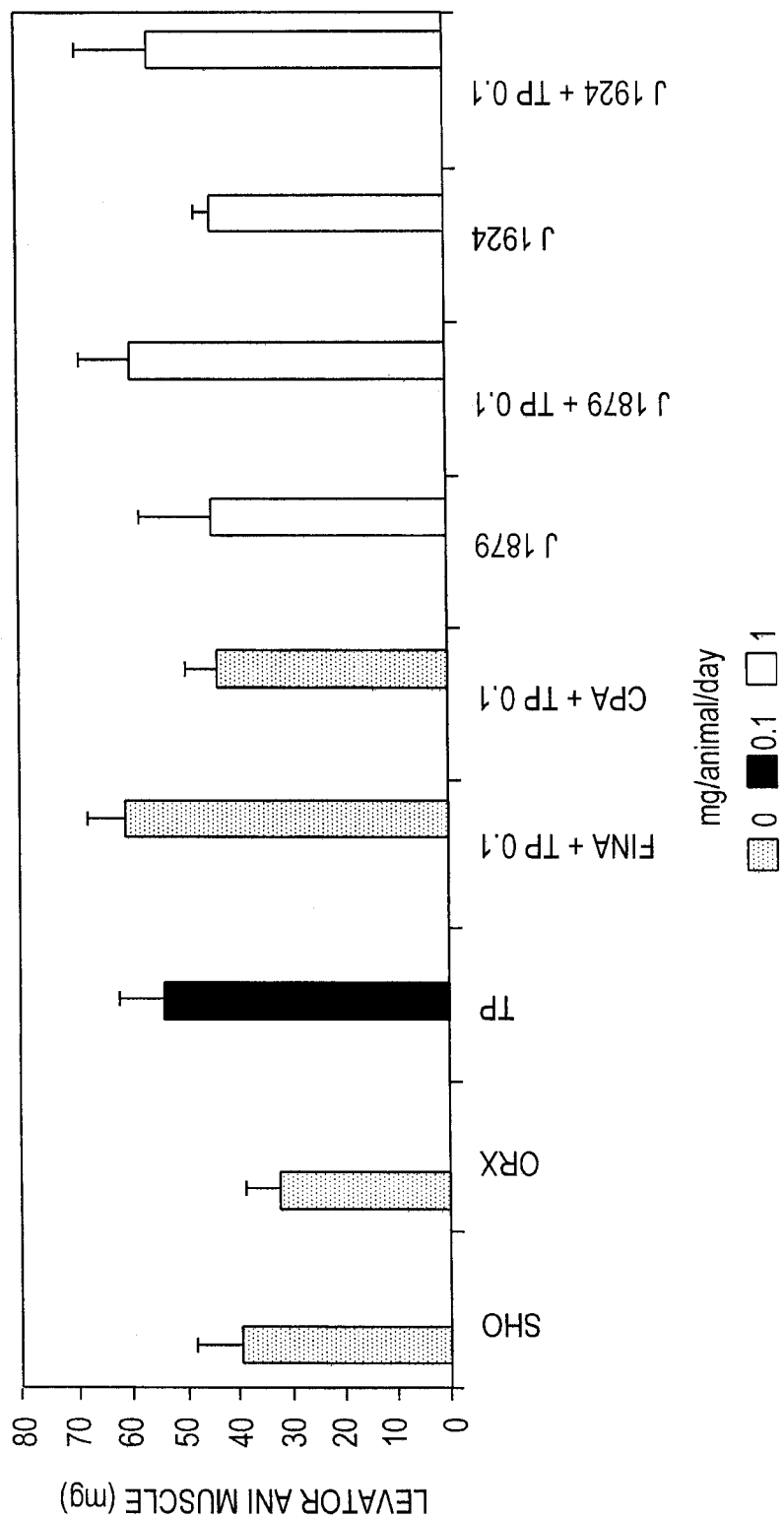
FIG. 2 is a graphical illustration comparing levator ani muscle weight in castrated infantile male rats after administration of 17-methylene-4-azasteroid compounds according to the invention with the levator ani muscle weight in the rats after administration of CPA and finasterides.
Figure 3:
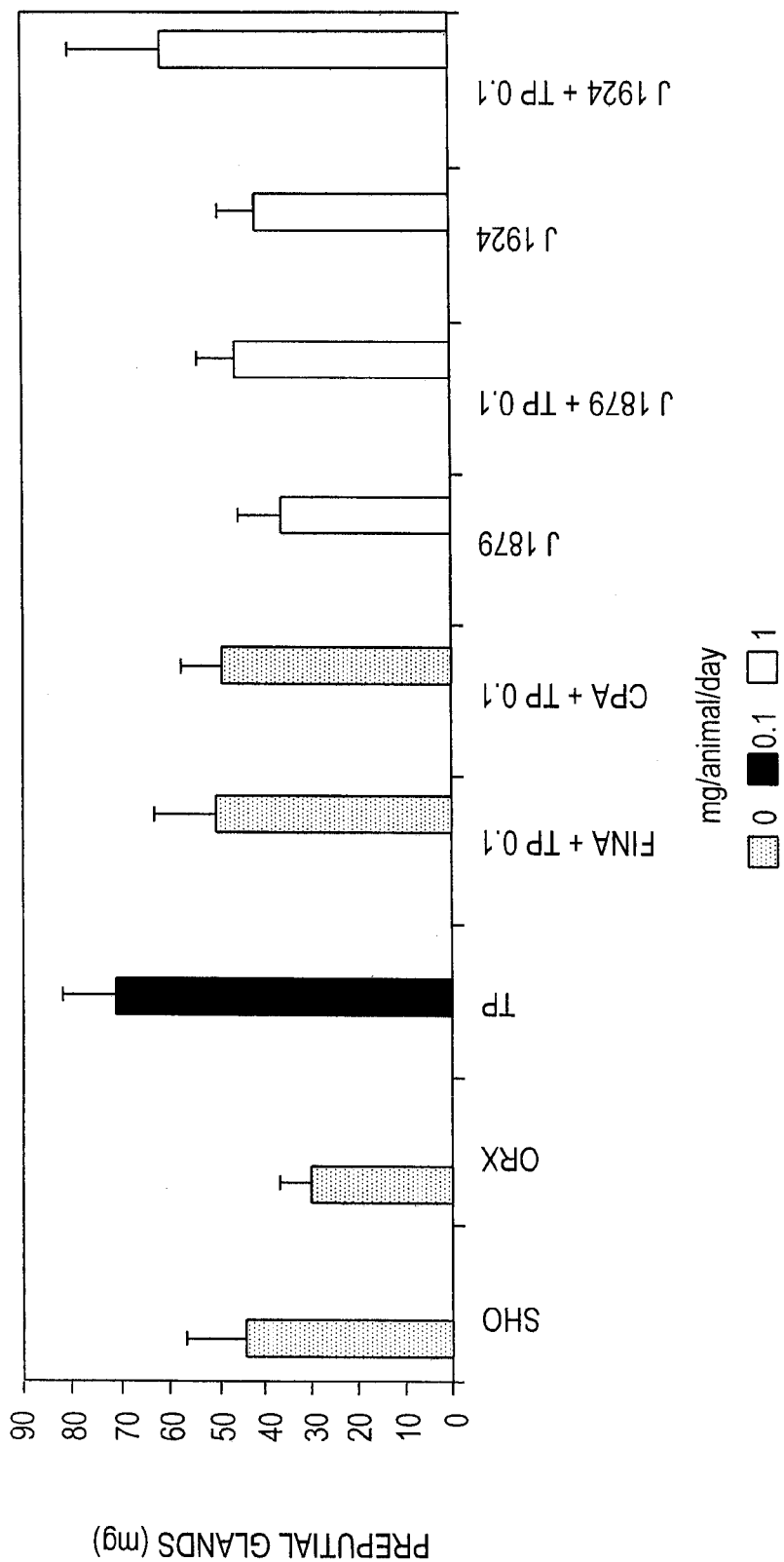
FIG. 3 is a graphical illustration comparing preputial gland weight in castrated infantile male rats after administration of 17-methylene-4-azasteroid compounds according to the invention with preputial gland weight in the rats after administration of CPA and finasterides.
Figure 4:
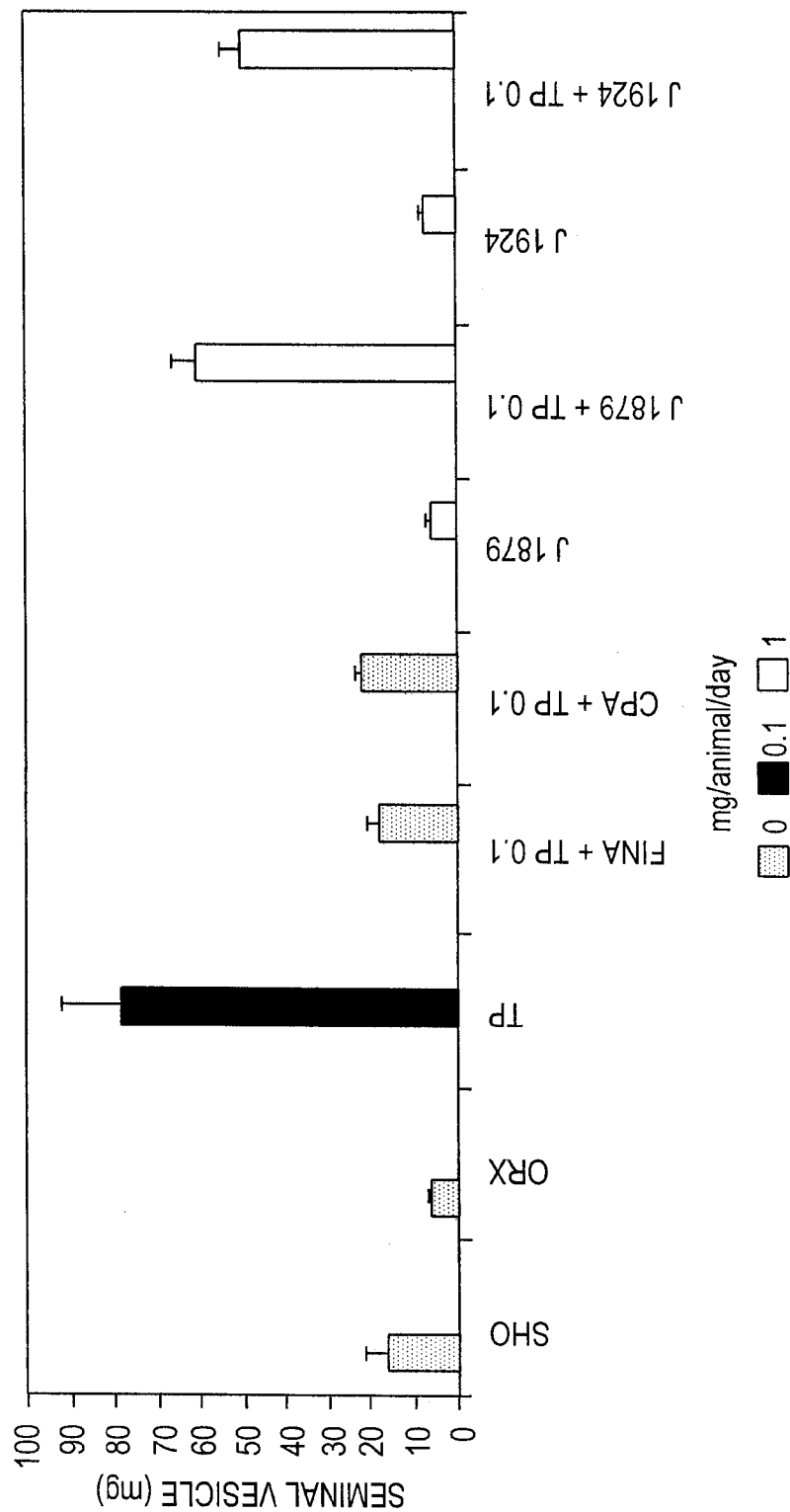
FIG. 4 is a graphical illustration comparing seminal vesicle weight in castrated infantile male rats after administration of 17-methylene-4-azasteroid compounds according to the invention with seminal vesicle weight in the rats after administration of CPA and finasterides.
Figure 5:
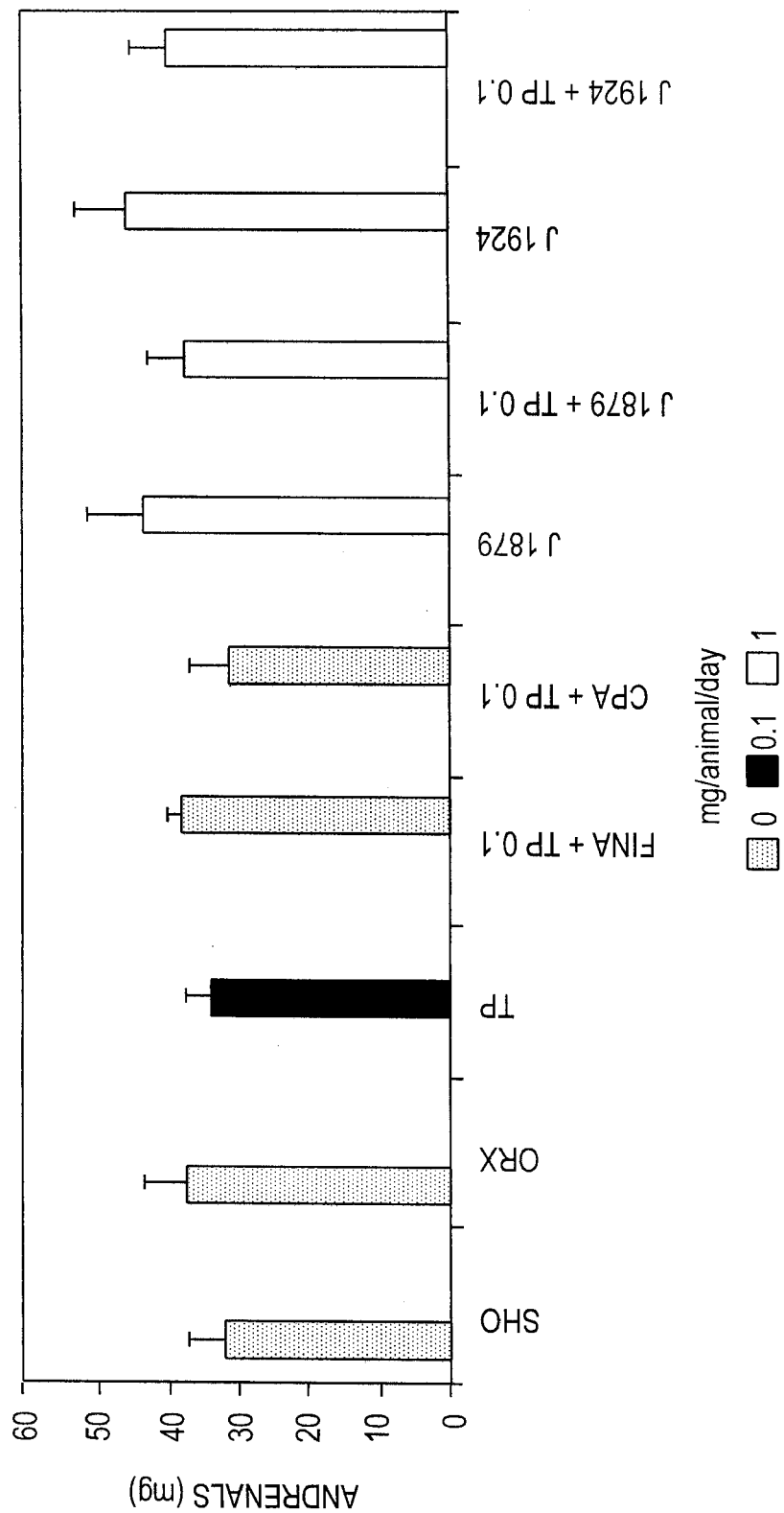
FIG. 5 is a graphical illustration comparing adrenal weight in castrated infantile male rats after administration of 17-methylene-4-azasteroid compounds according to the invention with the adrenal weight in the rats after administration of CPA and finasterides.

Evaluation of antiandrogenic activity of the compounds of the invention was performed in castrated male rats (see FIGS. 1 to 5/table). Castrated immature male rats were treated for 7 days with testosterone propionate (TP) and the substances of the invention (0.1 mg of TP alone and/or 1 mg of 5α-reductase inhibitor/animal/day, s.s., n=5–10/group). The treatment with TP caused a severe increase in weight of the accessory genital glands (prostate and seminal vesicle). In the animals treated with the vehicle and with 5α-reductase inhibitor alone, the weights of the examined organs remained at low values. The substances of the invention exerted an inhibitory effect in the test systems selected.

Table I shows that the compounds J 1879 and J 1924 appreciably reduced the effects of testosterone propionate, TP, on the prostate and seminal vesicle.

TABLE I

Inhibition of the action of testosterone propionate (TP) on the growth of the seminal vesicle and prostate. Test Performed on sexually immature, castrated male rats, n = 5–10/group, dosage: TP: 0.1 mg/animal/day s.c., 5α-reductase inhibitor: 1 mg/animal/day s.c., difference vehicle controls and TP controls = 100%.

| ET 01.31: | Prostate | Seminal vesicle |
|---|---|---|
| TP + J 1879 | 34 | 25 |
| TP + J 1924 | 39 | 41 |

The studies to determine the $IC_{50}$ values of the steroids J 1879 and J 1924 for the 5α-reductase outside the genital tract were carried out in four different human bone cells (hOB cells). The cells were incubated for 6 hours with 0.5 μM androstendione (0.1 μM [$^3$H] androstendione; 0.4 μM androstendione) with or without adding increasing concentrations of the inhibitor ($10^{-11}$–$10^{-8}$ M).

After the incubation, the medium was extracted with chloroform:methanol (2:1, vol:vol), the steroids (substrate and 5α-reduced metabolites) were separated by thin-layer chromatography, and the DNA content of the cells of the samples was determined. The 5α-reductase activity (sum of the 5α-reduced metabolites formed: 5α-androstandione, 5α-dihydrotestosterone, 5α-androstan-3α, 17β-diol, 5α-androstan-3β, 17β-diol expressed in pmol/μg DNA/h) was determined in duplicate samples. The relative 5α-reductase activity (5α-reductase activity of the samples with added inhibitor compared to the corresponding control values, namely those for the samples without added inhibitor) is shown in the figure always as a mean±SEM. The $IC_{50}$ values of J1879 and J1924 for the 5α-reductase in bone cells amounted to $<10^{-10}$ M in all cases.

In addition, within the framework of studies to determine the $IC^{50}$ values of J1879 and J1924, the inhibiting action of LY 191704, a nonsteroidal specific inhibitor of type-1 5α-reductase, finasteride, a 4-azasteroid with inhibiting action mainly on type-2 5α-reductase, and progesterone, a physiological substrate of 5α-reductase, was determined for comparative purposes in the four cell lines at a concentration of $10^{-8}$ M. It can be seen from the figures that the substances of the invention inhibited the 5α-reductase in the cell types studied more strongly and at substantially lower concentrations than did the natural substrates and reference substances.

The invention will be illustrated in greater detail by the following examples.

Example 1

E-17-Chloromethylene-4-aza-5α-androstan-3-one

To a solution of 3.1 mmol (1.0 g) of E-17-chloromethylene-4-aza-androst-5-en-3-one in 140 mL of dimethylformamide were added with stirring 59 mL of formic acid (85%) and 115.8 mmol (16 g) of potassium carbonate, and the reaction mixture was heated at reflux for 8 hours. Toluene was then added to the reaction solution, and the mixture was evaporated under vacuum. The residue was taken up in water, and the resulting mixture was extracted with methylene chloride. The combined extracts were treated with saturated sodium carbonate solution, washed neutral with water, dried over sodium sulfate and evaporated. The resulting crude product was crystallized from acetone/n-hexane, which gave 543 mg of solid product (54%).

M.p.=148–151° C.; $[\alpha]_D^{20}$=+16° (CHCl$_3$).

Example 2

E-17-Chloromethylene-4-methyl-4-aza-5α-androstan-3-one

To a suspension of 1.06 mmol (340 mg) of E-17-chloromethylene-4-aza-5α-androstan-3-one in 9 mL of dimethylformamide were added at room temperature and under an argon atmosphere 3.08 mmol (123 mg) of sodium hydride (60% in oil). The reaction mixture was stirred 30 mm, and to it was then added dropwise a solution of 5.3 mmol (0.33 mL) of methyl iodide in 3.0 mL of dimethylformamide. After about 60 minutes, 2 mL of methanol was added followed after another 10 mm by 9 mL of saturated aqueous ammonium chloride solution. The reaction mixture was diluted with water and extracted with toluene. The combined extracts were washed with water, dried over sodium sulfate and evaporated. The resulting crude produce was crystallized from acetone/n-hexane, which gave 154 mg of solid product (43%).

M.p.=150–162° C.; $[\alpha]_D^{20}$=–7° (CHCl$_3$).

Example 3

E-17-Chloromethylene-4-aza-5α-androst-1-en-3-one 1.34 mmol (430 mg) of E-17-chloromethylene-4-aza-5α-androstan-3-one was suspended in 9 mL of dioxane at room temperature and under an argon atmosphere and to the suspension were then added 1.5 mmol (340 mg) of 2,3-dichloro-5,6-dicyano-p-benzo-quinone and 6.4 mmol (1.7 mL) of bis-7-trimethyl-silyl)trifluoroacetamide. The mixture was stirred first 3 hours at room temperature and then 3 hours in an oil bath at about 100–110° C. The reaction solution was diluted with methylene chloride and then washed first with 2% aqueous sodium hydrogen sulfite solution, then with 2N hydrochloric acid and finally with water. The remaining extract was dried over sodium sulfate and evaporated. Crystallization from acetone gave 243 mg of solid product (57%).

M.p.=275–282° C.; $[\alpha]_D^{20}$=–41° (CHCl$_3$).

Example 4

E-17-Chloromethylene-4-methyl-4-aza-5α-androst-1-en-3-one

To a suspension of 0.87 mmol (279 mg) of E-17-chloromethylene-4-aza-5α-androst-1-en-3-one in 7 mL of dimethylformamide were added at room temperature and under an argon atmosphere 2.4 mmol (98 mg) of sodium hydride (60% in oil). The reaction mixture was stirred for 30 minutes, after which a solution of 7.5 mmol (0.47 mL) of methyl iodide in 3 mL of dimethylformamide was added dropwise. After about 60 minutes, 2 mL of methanol was added followed after an additional 10 mm by 9 mL of saturated aqueous ammonium chloride solution. The reaction mixture was diluted with water and extracted with toluene, and the extract was washed with water, dried over sodium sulfate and evaporated. The resulting crude product was crystallized from ethyl acetate, which gave 122 mg of solid product (42%).

M.p.=160–165° C.; $[\alpha]_D^{20}$=–47° (CHCl$_3$).

Example 5

E-17-Chloromethylene-4-aza-5α-estran-3-one

To a suspension of 3.27 mmol (1 g) of E-17-chloromethylene-4-aza-estr-5-en-3-one in 150 mL of dimethylformamide were added with stirring 73.3 mL of formic acid (85%) and 121.55 mmol (16.8 g) of potassium carbonate, and the reaction mixture was heated at reflux for 12 hours. Toluene was then added to the reaction solution, and the mixture was evaporated under vacuum. The residue was taken up in water and extracted with methylene chloride. The combined extracts were treated with saturated sodium carbonate solution, washed neutral with water, dried over sodium sulfate and evaporated. The resulting crude product was crystallized from acetone/n-hexane, which gave 461 mg of solid product (46%).

M.p.=(178–200) 262–282° C.; $[\alpha]_D^{20}$=–21° (CHCl$_3$).

Example 6

E-17-Chloromethylene-4-methyl-4-aza-5α-estran-3-one

To a suspension of 0.65 mmol (200 mg) of E-17-chloromethylene-4-aza-5α-estran-3-one in 5.8 mL of dimethylformamide were added at room temperature and under an argon atmosphere 1.7 mmol (73 mg) of sodium hydride (60% in oil). The reaction mixture was stirred 30 mm after which a solution of 3.2 mmol (0.2 mL) of methyl iodide in 2 mL of dimethylformamide was added dropwise. After about 60 minutes, 1 mL of methanol was added followed after an additional 10 mm by 4 mL of saturated aqueous ammonium chloride solution. The reaction mixture was diluted with water and extracted with methylene chloride.

The combined extracts were washed with water, dried over sodium sulfate and evaporated. The resulting crude product was purified by chromatography on Silica Gel 60 (eluent: methylene chloride/acetone 8/2). Crystallization from ethyl acetate then gave 131 mg of solid product (62%).

M.p.=161–171° C.; $[\alpha]_D^{20}$=−88° (CHCl$_3$).

Example 7

E-17-Chloromethylene-4-aza-5α-estr-1-en-3-one 1 mmol (310 mg) of E-17-chloromethylene-4-aza-5α-estran-3-one was suspended in 6.3 mL of dioxane at room temperature and under an argon atmosphere. Thereafter, 2.3 mmol (522 mg) of 2,3-dichloro-5,6-dicyano-p-benzoquinone and 9.8 mmol (2.6 mL) of bis-(trimethylsilyl)trifluoroacetamide were added. The mixture was stirred first 3 hours at room temperature and then 15 hours in an oil bath at 100–110° C. The reaction solution was diluted with methylene chloride and then washed first with 2% aqueous sodium hydrogen sulfite solution, then with 2N hydrochloric acid and finally with water. The remaining residue was dried over sodium sulfate and evaporated. Purification by chromatography on Silica Gel 60 (eluent: methylene chloride/methanol 98/2) gave 57 mg of solid product (18.5%).

$[\alpha]_D^{20}$=37° (CHCl$_3$).

The invention claimed is:

1. A 17-methylene-4-azasteroid compound of formula I:

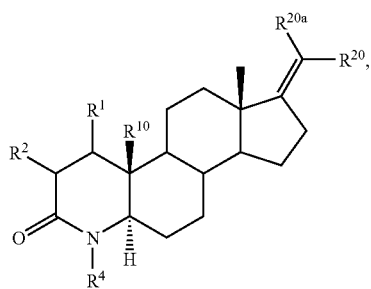

wherein
 $R^{20}$ denotes a fluoro, chloro, bromo, azido, cyano, thiocyanato, a $C_1$-$C_4$-alkyl or a hydroxy-$C_1$-$C_4$-alkyl group,
 $R^{20a}$ denotes hydrogen or a fluoro, chloro, bromo, azido, cyano, thiocyanato, a $C_1$-$C_4$-alkyl or a hydroxy-$C_1$-$C_4$-alkyl group,
 $R^{10}$ denotes a hydrogen atom or a methyl group,
 $R^4$ is selected from the group consisting of hydrogen and $C_1$-$C_4$-alkyl groups, and
 $R^1$ and $R^2$ each denote a hydrogen atom or together denote an additional bond.

2. The 17-methylene-4-azasteroid compound as defined in claim 1, wherein $R^4$=H or Me and wherein $R^{20}$ and $R^{20a}$, independently of each other, each denote F, Cl or Br.

3. The 17-methylene-4-azasteroid compound as defined in claim 1, selected from the group consisting of
 E-17-chloromethylene-4-aza-5α-estran-3-one,
 E-17-chloromethylene-4-aza-5α-androstan-3-one,
 E-17-chloromethylene-4-methyl-4-aza-5α-estran-3-one,
 E-17-chloromethylene-4-methyl-4-aza-5α-androstan-3-one,
 E-17-chloromethylene-4-aza-5α-estr-1-en-3-one,
 E-17-chloromethylene-4-aza-5α-androst-1-en-3-one,
 E-17-chloromethylene-4-methyl-4-aza-5α-androst-1-en-3-one,
 E-17-bromomethylene-4-methyl-4-aza-5α-estran-3-one,
 E-17-cyanomethylene-4-methyl-4-aza-5α-estran-3-one,
 Z-17-(1')-chloroethylidene-4-methyl-4-aza-5α-androstan-3-one,
 Z-17-(1')-chloroethylidene-4-methyl-4-aza-5α-estran-3-one,
 Z-17-(1')-bromoethylidene-4-methyl-4-aza-5α-androstan-3-one and
 Z-17-(1')-bromoethylidene-4-methyl-4-aza-5α-estran-3-one.

4. A process for making a 17-methylene-4-azasteroid compound of formula I:

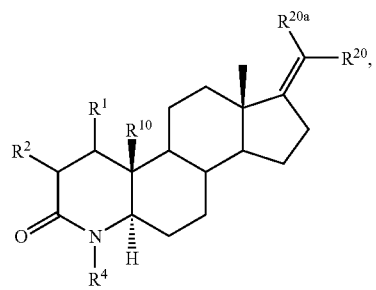

wherein $R^{20}$ is a fluoro, a chloro, a bromo group or a cyano group, $R^{20a}$ is hydrogen, $R^{10}$ denotes a hydrogen atom or a methyl group, $R^4$ is a methyl group, and $R^1$ and $R^2$ each denote a hydrogen atom; said process comprising the steps of:

a) reaching a 17-methylene steroid of formula II:

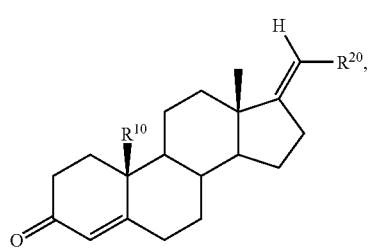

wherein $R^{10}$ denotes a hydrogen atom or a methyl group, and $R^{20}$ denotes a fluoro, a chloro, a bromo group or a cyano group, with NaIO$_4$ under catalytic mediation of KMnO$_4$ in a protic solvent to form a 3,5-seco-keto acid;

b) cyclizing said 3,5-seco-keto acid with NH$_4$OAc in glacial acetic acid to form an unsaturated lactam and then reducing said unsaturated lactam with HCOOH in DMF to a saturated lactam of formula III:

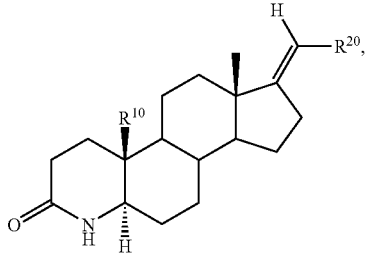

wherein R$^{10}$ and R$^{20}$ have the same meaning as in formula II, and c) reacting the saturated lactam of formula III with methyl iodide and NaH to form the 4-methyl-substituted compound of formula IV:

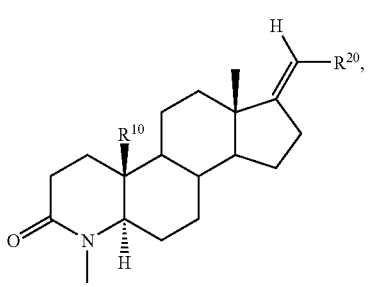

wherein R$^{10}$ and R$^{20}$ have the same meaning as in formula II.

5. A process for making a 17-methylene-4-azasteroid compound of formula I:

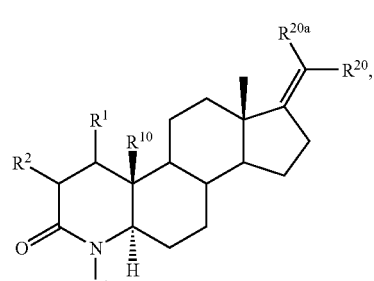

wherein R$^{20a}$ is a fluoro, a chloro, a bromo group or a cyano group, R$^{20}$ is a methyl group, R$^{10}$ denotes a hydrogen atom or a methyl group, R$^4$ is a methyl group, and R$^1$ and R$^2$ each denote a hydrogen atom; said process comprising the steps of:

a) reacting a 17-methylene steroid of formula VII:

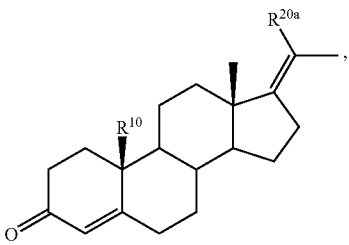

wherein R$^{10}$ denotes a hydrogen atom or a methyl group and R$^{20a}$ denotes a fluoro, a chloro, a bromo group or a cyano group,
with NaIO$_4$ under catalytic mediation of KMnO$_4$ in a protic solvent to form a 3,5-seco-keto acid;

b) cyclizing said 3,5-seco-keto acid with NH$_4$OAc in glacial acetic acid to form an unsaturated lactam and then reducing said unsaturated lactam with HCOOH in DMF to a saturated lactam of formula VIII:

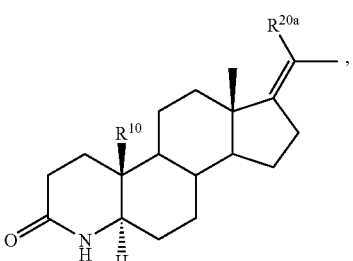

wherein R$^{10}$ and R$^{20a}$ have the same meaning as in formula VII, and c) reacting the saturated lactam of formula VIII with methyl iodide and NaH to form the 4-methyl-substituted compound of formula IX:

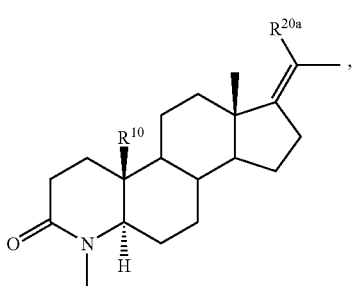

wherein R$^{10}$ and R$^{20a}$ have the same meaning as in formula VII.

6. A pharmaceutical composition comprising
a 17-methylene-4-azasteroid compound of formula I:

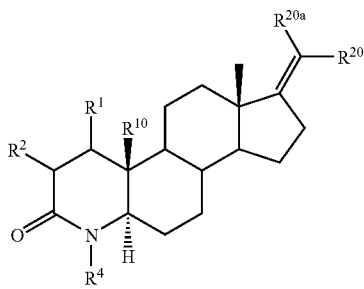

wherein $R^{20}$ denotes a fluoro, chloro, bromo, azido, cyano, thiocyanato, a $C_1$-$C_4$-alkyl or a hydroxy-$C_1$-$C_4$-alkyl group, $R^{20a}$ denotes hydrogen or a fluoro, chloro, bromo, azido, cyano, thiocyanato, a $C_1$-$C_4$-alkyl or a hydroxy-$C_1$-$C_4$-alkyl group, $R^{10}$ denotes a hydrogen atom or a methyl group, $R^4$ is selected from the group consisting of hydrogen and $C_1$-$C_4$-alkyl groups, and $R^1$ and $R^2$ each denote a hydrogen atom or together denote an additional bond; and at least one pharmaceutically compatible auxiliary agent and/or at least one pharmaceutically compatible carrier.

7. The pharmaceutical composition as defined in claim 6, wherein said 17-methylene-4-azasteroid compound is selected from the group consisting of
E-17-chloromethylene-4-aza-5α-estran-3-one,
E-17-chloromethylene-4-aza-5α-androstan-3-one,
E-17-chloromethylene-4-methyl-4-aza-5α-estran-3-one,
E-17-chloromethylene-4-methyl-4-aza-5α-androstan-3-one,
E-17-chloromethylene-4-aza-5α-estr-1-en-3-one,
E-17-chloromethylene-4-aza-5α-androst-1-en-3-one,
E-17-chloromethylene-4-methyl-4-aza-5α-androst-1-en-3-one,
E-17-bromomethylene-4-methyl-4-aza-5α-estran-3-one,
E-17-cyanomethylene-4-methyl-4-aza-5α-estran-3-one,
Z-17-(1')-chloroethylidene-4-methyl-4-aza-5α-androstan-3-one,
Z-17-(1')-chloroethylidene-4-methyl-4-aza-5α-estran-3-one,
Z-17-(1')-bromoethylidene-4-methyl-4-aza-5α-androstan-3-one and
Z-17-(1')-bromoethylidene-4-methyl-4-aza-5α-estran-3-one.

8. A method-of-treating acne, said method comprising the step of administering to an individual suffering from said acne an effective amount of at least one 17-methylene-4-azasteroid compound of formula I:

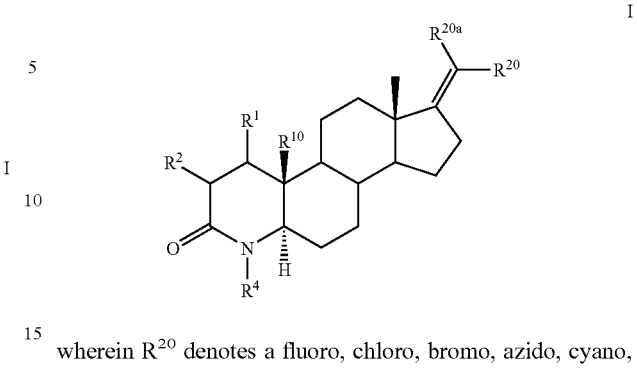

wherein $R^{20}$ denotes a fluoro, chloro, bromo, azido, cyano, thiocyanato, a $C_1$-$C_4$-alkyl or a hydroxy-$C_1$-$C_4$-alkyl group, $R^{20a}$ denotes hydrogen or a fluoro, chloro, bromo, azido, cyano, thiocyanato, a $C_1$-$C_4$-alkyl or a hydroxy-$C_1$-$C_4$-alkyl group, $R^{10}$ denotes a hydrogen atom or a methyl group, $R^4$ is selected from the group consisting of hydrogen and $C_1$-$C_4$-alkyl groups, and $R^1$ and $R^2$ each denote a hydrogen atom or together denote an additional bond.

9. A process for making a 17-methylene-4-azasteroid compound of formula I:

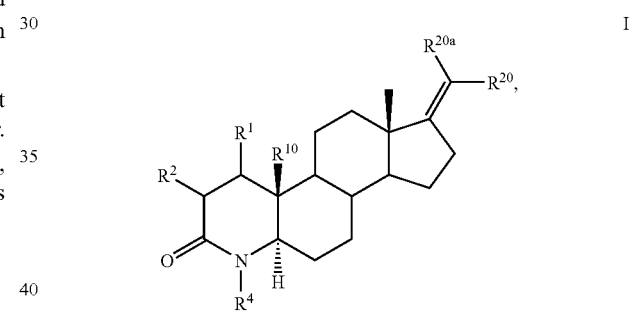

wherein $R^{20}$ is a fluoro, a chloro, a bromo group or a cyano group, $R^{20a}$ is hydrogen, $R^{10}$ denotes a hydrogen atom or a methyl group, $R^4$ is a methyl group, and $R^1$ and $R^2$ together denote an additional bond; said process comprising the steps of:
a) reacting a 17-methylene steroid of formula II:

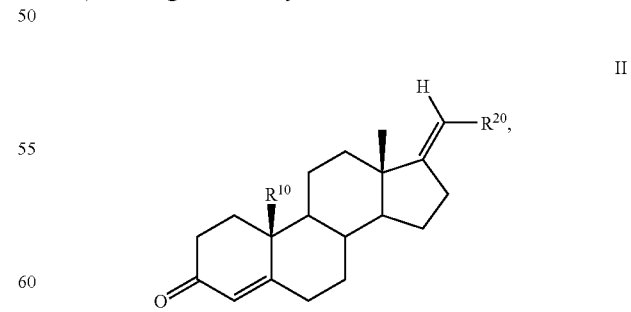

wherein $R^{10}$ denotes a hydrogen atom or a methyl group, and $R^{20}$ denotes a fluoro, a chloro, a bromo group or a cyano group,
$NaIO_4$ under catalytic mediation of $KMnO_4$ in a protic solvent to form a 3,5-seco-keto acid;

b) cyclizing said 3,5-seco-keto acid with NH$_4$OAc in glacial acetic acid to form an unsaturated lactam and then reducing said unsaturated lactam with HCOOH in DMF to a saturated lactam of formula III:

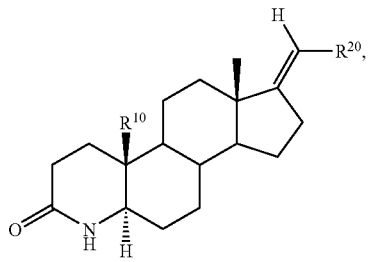

III wherein R$^{10}$ and R$^{20}$ have the same meaning as in formula II;

c) reacting the saturated lactam of formula III in a silyl-mediated 2,3-dichloro-5,6-dicyano-1,4-benzoquinone oxidation to form a dehydrogenated compound of formula V:

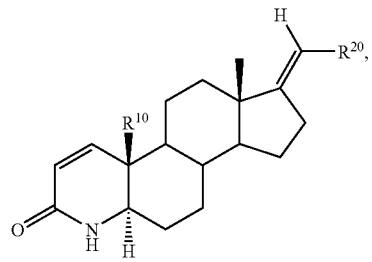

V wherein R$^{10}$ and R$^{20}$ have the same meaning as in formula II; and d) reacting the dehydrogenated compound of formula V with methyl iodide and NaH to form a 4-methyl-substituted compound of formula VI:

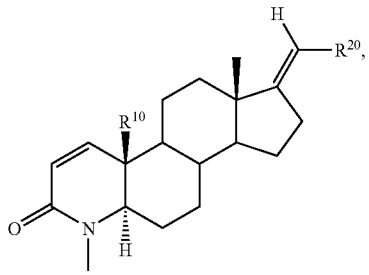

VI wherein R$^{10}$ and R$^{20}$ have the same meaning as in formula II.

10. A process for making a 17-methylene-4-azasteroid compound of formula I:

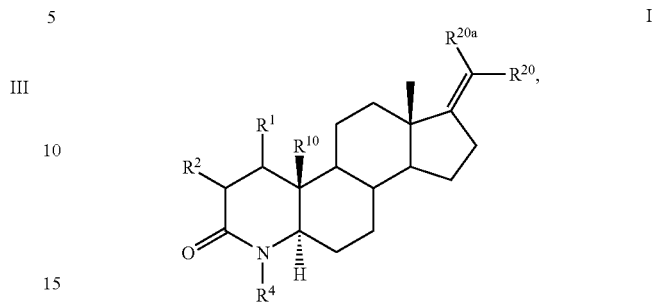

I wherein R$^{20a}$ is a fluoro, a chloro, a bromo group or a cyano group, R$^{20}$ is a methyl group, R$^{10}$ denotes a hydrogen atom or a methyl group, R$^4$ is a methyl group, and R$^1$ and R$^2$ together denote an additional bond; said process comprising the steps of:

a) reacting a 17-methylene steroid of formula VII:

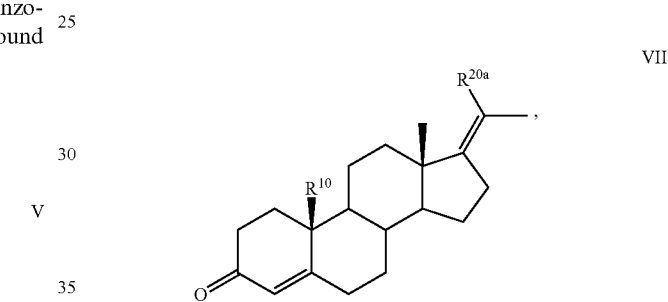

VII wherein R$^{10}$ denotes a hydrogen atom or a methyl group, and R$^{20a}$ denotes a fluoro, a chloro, a bromo group or a cyano group, with NaIO$_4$ under catalytic mediation of KMnO$_4$ in a protic solvent to form a 3,5-seco-keto acid;

b) cyclizing said 3,5-seco-keto acid with NH$_4$OAc in glacial acetic acid to form an unsaturated lactam and then reducing said unsaturated lactam with HCOOH in DMF to a saturated lactam of formula VIII:

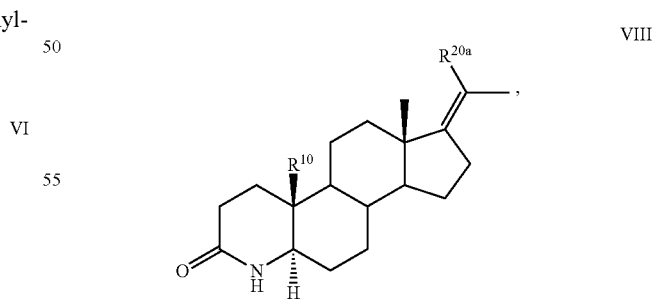

VIII wherein R$^{10}$ and R$^{20a}$ have the same meaning as in formula VII;

c) reacting the saturated lactam of formula VIII by silyl-mediated 2,3-dichloro-5,6-dicyano-1,4-benzoquinone oxidation to form a dehydrogenated compound of formula X:

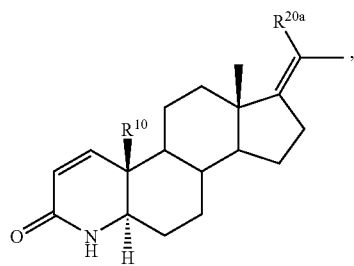
X
wherein $R^{10}$ and $R^{20a}$ have the same meaning as in formula VII; and
d) reacting the dehydrogenated compound of formula X with methyl iodide and NaH to form a 4-methyl-substituted compound of formula XI:
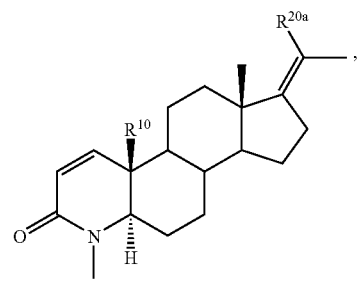
XI
wherein $R^{10}$ and $R^{20a}$ have the same meaning as in formula VII.
* * * * *